United States Patent
Sha

(10) Patent No.: US 12,342,775 B2
(45) Date of Patent: Jul. 1, 2025

(54) RICE CULTIVAR 'TAURUS'

(71) Applicant: The Board of Trustees of the University of Arkansas, Little Rock, AR (US)

(72) Inventor: Xueyan Sha, Stuttgart, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 292 days.

(21) Appl. No.: 18/077,855

(22) Filed: Dec. 8, 2022

(65) Prior Publication Data

US 2024/0188524 A1   Jun. 13, 2024

(51) Int. Cl.
*A01H 6/46* (2018.01)
*A01H 5/10* (2018.01)

(52) U.S. Cl.
CPC ............ *A01H 6/4636* (2018.05); *A01H 5/10* (2013.01)

(58) Field of Classification Search
None
See application file for complete search history.

(56) References Cited

U.S. PATENT DOCUMENTS

| | | |
|---|---|---|
| 6,281,416 B1 | 8/2001 | Moldenhauer |
| 7,429,697 B2 | 9/2008 | Moldenhauer |
| 8,134,058 B2 | 3/2012 | Moldenhauer |
| 9,398,750 B2 | 7/2016 | Moldenhauer et al. |
| 9,877,452 B1 * | 1/2018 | Moldenhauer ..... C12N 15/8274 |
| 10,791,697 B2 | 10/2020 | Wisdom et al. |
| 2022/0095561 A1 | 3/2022 | Moldenhauer |
| 2022/0104447 A1 | 4/2022 | Moldenhauer |
| 2022/0125000 A1 | 4/2022 | Sha |
| 2022/0132766 A1 | 5/2022 | Moldenhauer |

OTHER PUBLICATIONS

Schnell et al (A comparative analysis of insertional effects in genetically engineered plants: considerations for pre-market assessments. Transgenic research 24: 1-17, 2015) (Year: 2015).*
Fu et al (Unintended effects of transgenic rice revealed by transcriptome and metabolism. GM Crops & Food, 10:20-34, 2019) (Year: 2019).*
University of Arkansas (Arkansas Agricultural Experiment Station, Row Crops-Rice, published May 1, 2021) (Year: 2021).*
U_Arkansas_Taurus_May 2021_publish_date (Year: 2021).*
University of Arkansas (Arkansas_Rice_Performance_Trials_Dec. 2021) (Year: 2021).*
Bollich, C.N. et al. 1990. Registration of 'Rico 1' rice. Crop Science 30:1161.
Linscombe, S.D., et al. 1993. Registration of 'Bengal' rice. Crop Science 33:645-646.
Linscombe, S.D., et al. 2001. Registration of 'Earl' rice. Crop Science 41:2003-2004.
McKenzie, K.S., et al. 1988. Registration of 'Mercury' rice. Crop Science 28:193-194.
U.S. Plant Variety Protection Application No. 202300077 filed Nov. 23, 2022, Rice Cultivar 'Taurus', The Board of Trustees of the University of Arkansas.
U.S. Appl. No. 17/974,059, filed Oct. 26, 2022, Rice Cultivar Aroma 22, The Board of Trustees of the University of Arkansas.
U.S. Appl. No. 18/073,277, filed Dec. 1, 2022, Rice Cultivar 'Ozark', Debra Ahrent Wisdom, et al. inventor, The Board of Trustees of the University of Arkansas.
U.S. Plant Variety Protection Certificate No. 201700102, dated Jan. 29, 2020, The Board of Trustees of the University of Arkansas.

* cited by examiner

*Primary Examiner* — Charles Logsdon
*Assistant Examiner* — Wayne Zhong
(74) *Attorney, Agent, or Firm* — Quarles & Brady, LLP

(57) ABSTRACT

A rice cultivar designated Taurus is disclosed herein. The present invention provides seeds, plants, and plant parts derived from rice cultivar Taurus. Further, it provides methods for producing a rice plant by crossing Taurus with itself or another rice variety. The invention also encompasses any rice seeds, plants, and plant parts produced by the methods disclosed herein, including those in which additional traits have been transferred into Taurus through the introduction of a transgene or by breeding Taurus with another rice cultivar.

20 Claims, No Drawings

RICE CULTIVAR 'TAURUS'

BACKGROUND OF THE INVENTION

The present invention relates to a new and distinctive rice cultivar, designated 'Taurus'. Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valley of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season. In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in regions where rice is drill-seeded and a water-seeded nursery is used in regions where water-seeding is prominent.

Rice in the United States is classified into three primary market types by grain size, shape and chemical composition of the endosperm: long-grain, medium-grain, and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a new and distinct rice cultivar designated 'Taurus'. The invention encompasses the seeds, plants, and plant parts of rice cultivar Taurus, as well as plants with all the physiological and morphological characteristics of Taurus.

This invention also provides methods for producing a rice plant by planting a plurality of seeds or by crossing rice cultivar Taurus with itself or another rice line. Any plant breeding methods using rice cultivar Taurus are part of this invention, including selfing, backcrosses, hybrid production, and crosses to populations. All plants and seeds produced using rice cultivar Taurus as a parent are within the scope of this invention, including gene-converted plants of Taurus. Methods for introducing a gene into Taurus, either through traditional breeding or transformation, are also provided herein.

In still another aspect, the present invention provides regenerable cells for use in tissue culture of rice plant Taurus, as well as rice plants regenerated from these tissue cultures.

Definitions

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be backcrossed with one of the parental lines used to produce the $F_1$ hybrids.

Breeding. The genetic manipulation of living organisms.

Cell. A cell is the basic structural unit of all organisms. As used herein, this term includes isolated cells, cells grown in tissue culture, and cells that comprise a plant or plant part.

Cultivar. Used interchangeably with "variety". Refers to plants that have been cultivated by humans that have the characteristics of a particular genotype or combination of genotypes. Plants of a particular cultivar are distinguished from any other plants by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem, and leaves.

Essentially all the physiological and morphological characteristics. A plant having essentially all the physiological and morphological characteristics of the cultivar exhibits the characteristics of the cultivar with the exception of any characteristics derived from a converted gene.

$F_{\#}$. Denotes a filial generation, wherein the # is the generation number. For example, $F_1$ is the first filial generation.

Gene. Refers to a unit of inheritance corresponding to a distinct DNA sequence that forms part of a chromosome. A gene may encode a polypeptide or a functional nucleic acid molecule.

Gene-converted. Describes a plant wherein essentially all the desired physiological and morphological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernal length (L). Length of a rice grain measured in millimeters.

Kernal width (W). Width of a rice grain measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength."

Milling yield. A measure of the amount of rice kernels recovered after milling (i.e., the removal of hulls, bran, and germ). Milling yield is often expressed as a ratio of the amount of head rice (i.e., whole kernels) to the total amount of milled rice (i.e., whole and broken kernels). Both values are expressed as a weight percentage of the original paddy or rough rice sample that was milled. For example, for a sample of 100 grams of rough rice, a milling yield of 65:70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an $F_1$ rice plant produced from the cross of two rice plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like.

Trait. Refers to a measurable and/or observable characteristic of an organism.

Transgenic. Describes an organism or cell that contains genetic material that has been artificially introduced.

Wild-type. Used to refer to a gene that is common throughout a population and is, thus, arbitrarily designated the "normal" or "wild-type" form of the gene.

DETAILED DESCRIPTION OF THE INVENTION

The present invention provides a new and distinct rice cultivar designated 'Taurus'. The invention encompasses both the seeds of this cultivar and plants grown from these seeds. The invention further encompasses any rice plant having essentially all the physiological and morphological characteristics rice cultivar Taurus.

Development and Characterization of Rice Cultivar Taurus:

Taurus (Poaceae Oryzea *Oryza sativa* L.) is a high yielding, very early maturing, short stature, medium-grain rice cultivar developed in Stuttgart, Arkansas. It was originally selected from the cross 'Rico 1'/'Bengal'//RU0602162/ RU0502031 made in spring 2013. RU0602162 (pedigree Bengal//'Mercury'/Rico 1/3/'Earl') and RU0502031 (pedigree Bengal//Mercury/Rico 1/3/Mercury/Rico 1//Bengal) are unreleased, southern, medium-grain rice experimental lines. Rico 1 is a high yielding, midseason, conventional height, medium-grain rice cultivar. Bengal, Earl, and Mercury are southern, medium-grain rice cultivars (Linscombe et al, 1993; Linscombe et al, 2001; Mckenzie et al, 1988).

Taurus was initiated as an $F_4$ bulk of single progeny row 16P36262 in summer 2016. It was evaluated in the 2017 Stuttgart Initial Trial (SIT) as entry 17SIT803, where it ranked $1^{st}$ among 186 medium-grain experimental lines and checks. It was advanced to the Advanced/Elite Line Yield Trial (AYT) as entry 18AYT76 in 2018, as well as the Arkansas Rice Performance Trial (ARPT) and the Cooperative Uniform Regional Rice Nursery (URRN) in 2019 with the experimental designation RU1901033.

Taurus has an outstanding yield potential, good milling and grain quality, and improved lodging and blast resistance compared with the current commercial cultivar 'Jupiter' (Plant Variety Certificate No. 200500285). In 38 statewide and regional trials during 2018-2021, Taurus yielded an average 219 bushels/acre at 120 g $kg^{-1}$ moisture which compares favorably with the 206 bushels/acre yielded by 'Titan' (Plant Variety Certificate No. 201700102). Average milling yields (g $kg^{-1}$ whole milled kernels: g $kg^{-1}$ total milled rice) were 641:708 for Taurus and 622:700 for Titan. Taurus has a semi-dwarf plant type and is moderately susceptible to lodging. It averaged 34 inches in height in yield tests across the Mid-South, which is slightly shorter than Jupiter and about 3 inches shorter than Titan. Taurus matures 2 days earlier than Jupiter and 3 days later than Titan. The average number of days from emergence to 50% heading for Taurus is 85 as compared to 89 for Jupiter and 83 for Titan.

Taurus is a typical Southern medium-grain variety. Its kernels are plumper and longer than those of Jupiter but slightly smaller than those of Titan. Based on the analyses conducted by Riceland Foods (Stuttgart, AR) on 16 different sets of samples collected across Arkansas during 2019-2020, the length (mm), width (mm), length/width ratio, and kernel weight (mg) of milled whole kernels of Taurus were 5.89, 2.49, 2.37, and 20.80, respectively, as compared to 5.57, 2.67, 2.16, and 21.36 for Jupiter, and 6.06, 2.59, 2.34, and 22.50 for Titan. Average apparent amylose content of Taurus is 142 g kg$^{-1}$ compared to 145 for Jupiter and 152 for Titan. Taurus also has a low gelatinization temperature of 61.6° C., which is slightly lower than that of Jupiter (63.3° C.) and Titan (62.1° C.). Taurus has a low chalkiness value of 1.6%, which is lower than that of both Jupiter (2.6%) and Titan (1.7%).

Under both inoculated and natural infestation conditions, Taurus was rated moderately susceptible to leaf blast (caused by *Pyricularia grisea* (Cooke) Sacc.), which is an improvement over Jupiter which was rated susceptible. Molecular markers confirmed that Taurus possesses both blast resistant genes Pi-z and Pi-ks, whereas Jupiter possesses only a single gene (i.e., Pi-ks). In a greenhouse inoculated test, Taurus was found to be susceptible to blast races IB-1, IB-33, and IB-49, but resistant to IC-17 and IE-1. Under natural infestation or inoculated conditions, Taurus appears to be susceptible to sheath blight (caused by *Rhizoctonia solani* Kühn) and bacterial panicle blight (caused by *Burkholderia glumae*).

The leaves, lemma, and palea of Taurus are glabrous. The spikelet is straw colored. The apiculus is purple at heading and straw color as the grains approach maturity. The grain is non-aromatic.

Variants observed and removed from fields of Taurus were primarily taller and earlier. Other variants included any combination of the following: pubescent, later, shorter, long-grain, short-grain, intermediate-grain, gold or back hull, and sterile panicle. The total number of variants numbered less than 1 per 2000 plants.

The above-mentioned characteristics of rice cultivar Taurus are based primarily on data collected in Stuttgart, Arkansas and are summarized in Table 1. The developmental timeline for Taurus is shown in Table 2. The results of the rice performance trials (ARPT 2019-2021, URRN 2019-2021, and AYT 2018-2021) are detailed in Tables 3-17. Disease evaluation data is shown in Tables 18-20. The data were collected from the Advanced Elite Line Yield Trial (AYT) at RREC near Stuttgart, Pine Tree Experiment Station (PTST) near Colt, AR, and Northeast Research and Extension Center (NEREC) in Keiser; and URRN in Crowley, LA, Stuttgart, AR, Stoneville, MS, Malden, MO (2020 only), and Beaumont, TX; ARPT in Clay Co., Desha Co., RREC, Stuttgart, PTST, NEREC, Northeast Rice Research and Extension Center (NERREC, 2021 only), and Malden, MO (2020 only).

TABLE 1

Cultivar description information

Plant:

Grain type: Medium
Days to maturity (Seeding to 50% heading): 85
Plant height: 87 cm
Plant color at booting: Dark green Culm:

Angle (degrees from perpendicular after flowering): Erect (less than 30°)
Flag leaf (after heading):
Pubescence: Glabrous
Leaf angle: Erect
Blade color: Dark green TABLE 1-continued Cultivar description information Panicle:

Length: 21.6 cm
Type: Compact
Exertion (near maturity): Moderately well
Axis: Droopy
Shattering (at maturity): Low (1-5%)
Grain (spikelet):

Awns (after full heading): Absent
Apiculus color: Purple
Stigma color: White
Lemma and palea color (at maturity): Straw
Lemma and palea pubescence: Glabrous
Grain (seed):

Seed coat color: Light brown
Scent: Nonscented
Size: 25.4 g/1000 seeds milled rice
Shape class (length/width ratio):

Paddy: Medium (2.3:1 to 3.3:1)
Brown: Medium (2.1:1 to 3.0:1)
Milled: Medium (2.0:1 to 2.9:1)
Disease resistance:

Rice blast (*Pyricularia grisea* (Cooke) Sacc.): Moderately susceptible
Sheath blight (*Rhizoctonia solani* Kuhn): Susceptible
False smut (*Ustilaginoidea virens* (Cooke) Takah.): Susceptible
Bacterial panicle blight (*Burkholderia glumae* and *B. gladioli*): Susceptible

TABLE 2

Development timeline of Taurus

| Year | Generation | Designation | Trials | Comments |
|---|---|---|---|---|
| 2013 | Cross | 13CRS257 | | Spring 2013 |
| 2013 | F1 | 13TP649 | Transplant | |
| 2014 | F2 | 14SP529 | Space-planted F$_2$ Population | |
| 2015 | F3 | 15P60045 | Progeny Row | |
| 2016 | F4 | 16P36262 | Progeny Row, Bulk | |
| 2017 | F5 | 17SIT803 | Stuttgart Initial Trials (SIT) | |
| 2018 | F6 | 18AYT76 | Advanced/Elite Line Yield Trial (AYT) | |
| 2019 | F7 | RU1901033 | Uniform Regional Rice Nursery (URRN) | |
| 2019 | F7 | 19ARPT E272 | Arkansas Rice Performance Trial (ARPT) | |
| 2019 | F7 | 19AYT76 | AYT | |
| 2020 | F8 | RU1901033 | URRN | |
| 2020 | F8 | 20ARPT E141 | ARPT | |
| 2020 | F8 | 20AYT76 | AYT | |
| 2021 | F9 | RU1901033 | URRN | |
| 2021 | F9 | 21ARPT E53 | ARPT | |
| 2021 | F9 | 21AYT76 | AYT | |
| 2021-22 | F10 | RU1901033 | Breeder Headrow Increase | Puerto Rico |
| 2022 | F11 | RU2001185 | Foundation Seed Production | |

TABLE 3

Overall average grain yield (at 12% H₂O) and milling yields
(% head and total rice), 2018-2021

| Cultivar | Grain Yield (Bu/A) | Grain Yield (lb/A) | Milling Yield (%) Head Rice | Total Rice |
|---|---|---|---|---|
| Taurus | 219 | 9,848 | 63.4 | 70.4 |
| Jupiter | 212 | 9,521 | 63.1 | 68.3 |
| Titan | 206 | 9,274 | 61.6 | 69.9 |
| No. trials | 42 | 42 | 40 | 40 |

TABLE 4

Overall average days to 50% heading, plant
height, and lodging incidence, 2018-2021

| Cultivar | Days to 50% heading | Plant height (inch) | Lodging incidence (%) |
|---|---|---|---|
| Taurus | 85 | 34 | 6.9 |
| Jupiter | 89 | 37 | 3.4 |
| Titan | 83 | 37 | 2.9 |
| No. trials | 41 | 42 | 42 |

TABLE 5

Kernel dimension and weight of milled rice analyzed by
Riceland Foods, Inc., Stuttgart, Arkansas using ARPT
samples collected across the state, 2019-2020

| Cultivar | Length (L) mm | Width (W) mm | Thickness mm | L/W ratio | Kernel weight (mg) |
|---|---|---|---|---|---|
| Taurus | 5.89 | 2.49 | 1.79 | 2.37 | 20.80 |
| Jupiter | 5.67 | 2.63 | 1.85 | 2.16 | 21.36 |
| Titan | 6.06 | 2.59 | 1.80 | 2.34 | 22.50 |
| No. trials | 16 | 16 | 16 | 16 | 16 |

TABLE 6

Rapid Viscosity Analysis (RVA) results measured in Rapid-Visco
Analyser units (RVU) analyzed by Riceland Foods, Inc., Stuttgart,
Arkansas using ARPT samples collected across the state, 2019-2020

| Cultivar | Peak Viscosity | Trough | Breakdown | Final Viscosity | Setback |
|---|---|---|---|---|---|
| Taurus | 274 | 135 | 139 | 223 | −50 |
| Jupiter | 231 | 130 | 112 | 207 | −25 |
| Titan | 256 | 123 | 133 | 210 | −45 |
| No. trials | 14 | 14 | 14 | 14 | 14 |

TABLE 7

Average grain yield in the ARPT at
six Arkansas locations, 2019-2021

| | Grain yield (bushels/acre at 12% H₂O) | | | | | | |
|---|---|---|---|---|---|---|---|
| Cultivar | Clay† | Desha | NEREC | NRREC | PTRS | RREC | Mean |
| Taurus | 253 | 218 | 224 | 246 | 200 | 225 | 223 |
| Titan | 240 | 197 | 214 | 206 | 184 | 207 | 208 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR. Each year, trials were conducted at all locations except for Desha (2020-2021) and NRREC (2021 only).

TABLE 8

Average milling yields in the ARPT at
six Arkansas locations, 2019-2021

| | Milling yields (% head rice-% total rice) | | | | | | |
|---|---|---|---|---|---|---|---|
| Cultivar | Clay† | Desha | NEREC | NRREC | PTRS | RREC | Mean |
| Taurus | 64-71 | 66-70 | 67-71 | 67-71 | 57-70 | 61-70 | 63-71 |
| Titan | 59-71 | 64-70 | 67-70 | 66-71 | 53-69 | 61-69 | 61-70 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR. Each year, trials were conducted at all locations except for Desha (2020-2021) and NRREC (2021 only).

TABLE 9

Overall agronomical characteristics in the
ARPT at six Arkansas locations, 2019-2021

| Cultivar | Days to 50% heading | Height (inch) | Lodging (%) |
|---|---|---|---|
| Taurus | 85 | 34 | 1.0 |
| Titan | 83 | 37 | 0.5 |

TABLE 10

Grain yield in the 2021 ARPT at six Arkansas locations

| | Grain yield (bushels/acre at 12% H₂O) | | | | | | |
|---|---|---|---|---|---|---|---|
| Cultivar | Clay† | Desha | NEREC | NRREC | PTRS | RREC | Mean |
| Taurus | 249 | 205 | 238 | 246 | 210 | 241 | 232 |
| Titan | 227 | 202 | 236 | 206 | 175 | 221 | 211 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR

TABLE 11

Milling yields in the 2021 ARPT at six Arkansas locations

| | Milling yields (% head rice-% total rice) | | | | | | |
|---|---|---|---|---|---|---|---|
| Cultivar | Clay† | Desha | NEREC | NRREC | PTRS | RREC | Mean |
| Taurus | 57-70 | 65-71 | 68-72 | 68-72 | 62-70 | 58-70 | 63-71 |
| Titan | 46-69 | 65-71 | 68-71 | 66-71 | 53-69 | 58-69 | 59-70 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR

TABLE 12

Grain yield in the 2020 ARPT at five Arkansas locations

| | Grain yield (bushels/acre at 12% H₂O) | | | | | |
|---|---|---|---|---|---|---|
| Cultivar | Clay† | Desha | NEREC | PTRS | RREC | Mean |
| Taurus | 274 | 231 | 207 | 218 | 197 | 225 |
| Titan | 251 | 191 | 190 | 190 | 174 | 199 |

†Test location: Clay = Clay Co., AR., Desha = Desha Co., AR., NEREC = Northeast Research and Extension Center at Keiser, AR., PTRS = Pine Tree Research Station near Colt, AR., and RREC = Rice Research and Extension Center near Stuttgart, AR

TABLE 13

Milling yield in the 2020 ARPT at five Arkansas locations

Milling yields (% head rice-% total rice)

| Cultivar | Clay† | Desha | NEREC | PTRS | RREC | Mean |
|---|---|---|---|---|---|---|
| Taurus | 68-72 | 66-70 | 67-70 | 67-71 | 62-71 | 66-71 |
| Titan | 65-71 | 64-69 | 66-70 | 63-71 | 62-70 | 64-70 |

†Test location: Clay = Clay Co., AR., Desha = Desha Co., AR., NEREC = Northeast Research and Extension Center at Keiser, AR., PTRS = Pine Tree Research Station near Colt, AR., and RREC = Rice Research and Extension Center near Stuttgart, AR

TABLE 14

Grain yield in the 2019 ARPT at four Arkansas locations

Grain yield (bushels/acre at 12% H$_2$O)

| Cultivar | Clay† | NEREC | PTRS | RREC | Mean |
|---|---|---|---|---|---|
| Taurus | 235 | 227 | 171 | 238 | 218 |
| Jupiter | 200 | 230 | 198 | 246 | 218 |
| Titan | 235 | 222 | 190 | 228 | 219 |

†Test location: Clay = Clay Co., AR., NEREC = Keiser, AR., PTRS = Colt, AR., and RREC = Stuttgart, AR

TABLE 15

Milling yield in the 2019 ARPT at four Arkansas locations

Milling yields (% head rice-% total rice)

| Cultivar | Clay† | NEREC | PTRS | RREC | Mean |
|---|---|---|---|---|---|
| Taurus | 69-72 | 66-70 | 42-69 | 63-69 | 60-70 |
| Jupiter | 66-70 | 62-65 | 61-67 | 63-68 | 63-68 |
| Titan | 66-71 | 67-69 | 43-68 | 62-69 | 59-69 |

†Test location: Clay = Clay Co., AR., NEREC = Keiser, AR., PTRS = Colt, AR., and RREC = Stuttgart, AR.

TABLE 16

Average yield, milling, and agronomical characteristics in the URRN trials conducted in Stuttgart, AR, Crowley, LA, Stoneville, MS, Malden, MO, and Beaumont, TX, 2019-2021

| Cultivar | Days to 50% heading | Height (cm) | Lodging (%) | Yield (bu/A) | Yield (lb/A) | Head rice (%) | Total rice (%) |
|---|---|---|---|---|---|---|---|
| 2019-2021 Average | | | | | | | |
| Taurus | 87 | 90 | 20 | 202 | 9,089 | 61.9 | 70.3 |
| Jupiter | 91 | 98 | 7 | 205 | 9,219 | 62.2 | 68.2 |
| Titan | 85 | 102 | 8 | 206 | 9,268 | 60.9 | 69.5 |
| 2019 | | | | | | | |
| Taurus | 84 | 91 | 19 | 210 | 8989 | 66.2 | 72.3 |
| Jupiter | 88 | 100 | 0 | 200 | 9377 | 62.8 | 69.1 |
| Titan | 82 | 103 | 0 | 221 | 9,369 | 62.0 | 70.1 |
| 2020 | | | | | | | |
| Taurus | 88 | 90 | 36 | 200 | 8228 | 61.4 | 68.5 |
| Jupiter | 92 | 98 | 21 | 187 | 8789 | 61.8 | 67.5 |
| Titan | 87 | 101 | 21 | 181 | 9086 | 63.3 | 68.8 |
| 2021 | | | | | | | |
| Taurus | 88 | 91 | 0 | 210 | 10291 | 56.9 | 69.6 |
| Jupiter | 93 | 97 | 0 | 219 | 9559 | 62.0 | 67.9 |
| Titan | 86 | 101 | 4 | 233 | 9466 | 53.7 | 68.7 |

TABLE 17

Performance in the AYT conducted at Northeast Research and Extension Center (NEREC), Pine Tree Research Station (PTRS), and Rice Research and Extension Center (RREC), 2018-2021

| Cultivar | Seedling vigor† | Days to 50% heading | Plant height (inch) | Lodging (%) | Yield (bu/A) | Head rice (%) | Total rice (%) |
|---|---|---|---|---|---|---|---|
| 3-Location Average | | | | | | | |
| Taurus | 3.1 | 82 | 35 | 0 | 234 | 65.1 | 70.1 |
| Jupiter | 3.0 | 86 | 38 | 0 | 217 | 63.7 | 68.3 |
| Titan | 3.1 | 78 | 38 | 0 | 203 | 64.2 | 70.2 |
| RREC | | | | | | | |
| Taurus | 3.2 | 82 | 38 | 0 | 237 | 67.4 | 70.3 |
| Jupiter | 3.0 | 86 | 38 | 0 | 207 | 66.7 | 68.8 |
| Titan | 3.0 | 81 | 41 | 0 | 206 | 69.1 | 70.6 |
| PTRS | | | | | | | |
| Taurus | 3.0 | 82 | 33 | 0 | 229 | 63.4 | 70.1 |
| Jupiter | 3.0 | 85 | 35 | 0 | 227 | 62.2 | 67.6 |
| Titan | 3.0 | 77 | 35 | 0 | 201 | 62.9 | 69.9 |
| NEREC | | | | | | | |
| Taurus | 3.1 | 82 | 35 | 0 | 236 | 65.2 | 70.0 |
| Jupiter | 3.0 | 86 | 38 | 0 | 227 | 62.2 | 67.6 |
| Titan | 3.0 | 77 | 38 | 0 | 202 | 62.2 | 70.1 |

†Subjective rating 1-7, 1 = perfect stand and 7 = no stand.

TABLE 18

Average disease ratings (on a 0-9 scale, 0 = immune and 9 = maximum) under inoculation conditions, 2019

| Cultivar | Sheath blight | Leaf blast | Rotten neck blast | Bacterial panicle blight |
|---|---|---|---|---|
| Taurus | 8.3 | 7.3 | 5.3 | 7.5 |
| Jupiter | 6.8 | 6.8 | 2.5 | 2.5 |
| Titan | 6.3 | 6.8 | 3.5 | 6.7 |
| No. trials | 1 | 1 | 1 | 1 |

TABLE 19

Disease reactions of rice cultivars inoculated with different races of the blast pathogen (*Pyricularia oryzae*) a greenhouse in Stuttgart, AR, 2016

| Cultivar | IB-1 | IB-17 | IB-49 | IC-17 | IE1-K |
|---|---|---|---|---|---|
| Taurus | S† | S | MS | R | R |
| Jupiter | MS | S | S | MS | MS |
| Titan | S | S | MS | MR | MR |
| No. trials | 3 | 3 | 3 | 3 | 3 |

†Disease reaction, R = resistant, MR = moderately resistant, MS = moderately susceptible, and S = susceptible.

TABLE 20

Reactions of rice cultivar Taurus to diseases and lodging, 2021

| Sheath Blight | Blast | Straight-head | Bacterial Panicle Blight | Narrow Brown Leaf Spot | Stem Rot | Kernel Smut | False Smut | Lodging | Black Sheath Rot | Sheath Spot |
|---|---|---|---|---|---|---|---|---|---|---|
| S | MS | MR | — | MR | — | — | — | — | — | — |

Reaction:
R = Resistant;
MR = Moderately Resistant;
MS = Moderately Susceptible;
S = Susceptible;
VS = Very Susceptible Methods:

This present invention provides methods for producing rice plants. In some embodiments, these methods involve crossing a first parent rice plant with a second parent rice plant, wherein either the first or second parent rice plant is a Taurus rice plant. Further, both the first and second parent rice plants can come from rice cultivar Taurus. This invention is also directed to methods for producing a Taurus-derived rice plant by crossing rice cultivar Taurus with a second rice plant, growing the progeny seed, and repeating the crossing and growing steps with the Taurus-derived plant from 0 to 7 times. Any such methods using rice cultivar Taurus are part of this invention, including selfing, backcrosses, hybrid production, crosses to populations, and the like. All plants produced using rice cultivar Taurus as a parent are within the scope of this invention, including plants derived from rice cultivar Taurus. In some embodiments, rice cultivar Taurus is used in crosses with other, different, rice cultivars to produce first generation ($F_1$) rice seeds and plants with superior characteristics.

In some embodiments, a Taurus progeny plant is selected that has molecular markers, morphological characteristics, and/or physiological characteristics in common with Taurus (e.g., those listed in Table 1). Techniques such as RFLP-enhanced selection, genetic marker enhanced selection (e.g., SSR markers), and the making of double haploids may be utilized to identify progeny that share particular traits with Taurus.

Further, this invention provides methods for introducing a desired trait into rice cultivar Taurus. This may be accomplished using traditional breeding methods, such as back-crossing (see the section titled "Breeding Methods" below). Alternatively, the desired trait may be introduced by transforming the rice cultivar with a transgene (see the section title "Transformation Methods" below). The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps that involve producing rice seed from the resulting rice plants and/or planting the rice seed.

The present invention encompasses all plants and parts thereof produced by the methods described herein, as well as the seeds produced by these plants. Further, any plants derived from rice cultivar Taurus or produced from a cross using cultivar Taurus are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar Taurus comprising a combination of at least two traits of Taurus selected from those described in the Tables and Detailed Description of the Invention. The progeny rice plant should not be significantly different from Taurus for said traits, as determined at the 5% significance level when grown in the same environment. Those of skill in the art know how to compare a trait between two plant varieties to determine if there is a significant difference between them (Fehr and Walt, Principles of Cultivar Development, pp. 261-286 (1987)). Molecular markers or mean trait values may be used to identify a plant as progeny of Taurus. Alternatively, progeny may be identified through their filial relationship with rice cultivar Taurus (e.g., as being within a certain number of breeding crosses of rice cultivar Taurus). For example, progeny produced by the methods described herein may be within 1, 2, 3, 4, or 5 breeding crosses of rice cultivar Taurus.

Tissue Culture:

The present invention provides tissue cultures of regenerable cells or protoplasts produced from rice cultivar Taurus. As is well known in the art, tissue culture of rice can be used for the in vitro regeneration of a rice plant. Thus, such cells and protoplasts may be used to produce plants having all the physiological and morphological characteristics of rice variety Taurus. The rice plants regenerated by these methods are also encompassed by the present invention.

As used herein, the term "tissue culture" describes a composition comprising isolated plant cells or a collection of such cells organized into parts of a plant. Exemplary tissues for culture include protoplasts, calli, plant clumps, embryos, pollen, flowers, seeds, pods, leaves, stems, roots, root tips, and anthers. Culture of various rice tissues and regeneration of plants therefrom is well known in the art.

Breeding Methods:

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar Taurus in any plant breeding method is encompassed by the present invention. The choice of a breeding or selection method will depend on several factors, including the mode of plant reproduction, the heritability of the trait(s) being improved, and the type of cultivar used commercially (e.g., $F_1$ hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the Fa generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods:

As is noted above, the present invention provides plants and seeds of rice cultivar Taurus in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is a DNA molecule comprising a gene operatively linked to a regulatory element (e.g., a promoter) that drives its expression in a cell. The expression vector may contain one or more such gene/regulatory element combinations. The expression vector may also include additional sequences, such as a signal sequence or a tag, that modify the protein produced by the transgene.

Expression vectors typically include at least one genetic marker that allows transformed cells containing the vector to be recovered by selection. In some embodiments, negative selection (i.e., inhibiting the growth of cells that do not contain the selectable marker gene) is utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and green fluorescent protein (GFP).

Transgene expression is typically driven by operably linking the transgene to a promoter within the expression vector. However, other regulatory elements may also be used to drive transgene expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be tissue-specific, cell type-specific, inducible, or constitutive. Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch, et al., *Science*, 227:1229 (1985). Descriptions of *Agrobacterium* vector systems and methods for *Agrobacterium*-mediated gene transfer are provided by Gruber, et al., supra.

REFERENCES

Bollich, C. N., Webb, B. D., Marchetti, M. A., and Scott, J. E. 1990. Registration of Rico 1 rice. Crop Sci. 30:1161.
Linscombe, S. D., Jodari, F., Mckenzie, K. S., Bollich, P. K., Groth, D. E., White, L. M., Dunand, R. T., Sanders, D. E. 1993. Registration of 'Bengal' rice. Crop Sci. 33:645-646.

Linscombe, S. D., Jodari, F., Bollich, P. K., Groth, D. E., White, L. M., Chu, Q. R., Dunand R. T. and Sanders, D. E. 2001. Registration of 'Earl' rice. Crop Sci. 41:2003-2004.

Mckenzie, K. S., Bollich, P. K., Groth, D. E., Jodari, F., Robinson, J. F., and Rutger, J. N. 1988. Registration of 'Mercury' rice. Crop Sci. 28:193-194.

DEPOSIT INFORMATION

A deposit of the University of Arkansas Division of Agriculture Rice Research and Extension Center proprietary rice cultivar 'Taurus' disclosed above and recited in the appended claims has been made with the Provasoli-Guillard National Center for Marine Algae and Microbiota (NCMA) (60 Bigelow Drive, East Boothbay, ME 04544) and has been accepted under the terms of the Budapest Treaty. The date of deposit was May 1, 2023. The deposit of 625 seeds was taken from the same deposit maintained by the University of Arkansas Division of Agriculture Rice Research and Extension Center (2900 Hwy 130 E., Stuttgart, AR 72160) since prior to the filing date of this application. All restrictions will be irrevocably removed upon granting of a patent, and the deposit is intended to meet all of the requirements of 37 C.F.R. §§ 1.801-1.809. The NCMA Accession Number is 202305003. The deposit will be maintained in the depository for a period of thirty years, or five years after the last request, or for the enforceable life of the patent, whichever is longer, and will be replaced as necessary during that period.

What is claimed is:

1. A rice seed of the cultivar 'Taurus', a representative sample of seed of said cultivar having been deposited under National Center for Marine Algae and Microbiota Accession No. 202305003.

2. A rice plant, or a part thereof, produced by growing the seed of claim 1.

3. A rice plant, or a part thereof, having all the physiological and morphological characteristics of the rice plant of claim 2.

4. Pollen or an ovule of the plant of claim 2.

5. A method for producing rice plants, said method comprising planting a plurality of rice seeds as recited in claim 1 under conditions favorable for the growth of rice plants.

6. The method of claim 5, further comprising the step of producing rice seed from the resulting rice plants.

7. A rice seed produced by the method of claim 6.

8. A tissue culture of regenerable cells or protoplasts produced from the rice plant of claim 2.

9. The tissue culture of claim 8, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

10. A rice plant regenerated from the tissue culture of claim 8, said rice plant having all the physiological and morphological characteristics of 'Taurus'.

11. A method for producing an $F_1$ hybrid rice seed, said method comprising crossing a first parent rice plant with a second parent rice plant, wherein the first parent rice plant is the rice plant of claim 2, and the second parent rice plant is a different cultivar, to produce the $F_1$ hybrid rice seed.

12. The method of claim 11, further comprising the step of planting the $F_1$ hybrid rice seed to produce an $F_1$ hybrid rice plant.

13. A F1 hybrid rice seed produced by the method of claim 11.

14. The method of claim 11, wherein the second parent rice plant is transgenic.

15. A method comprising transforming the rice plant or part thereof of claim 2 with a transgene, wherein the transgene confers at least one trait selected from the group consisting of: herbicide resistance, insect resistance, resistance to bacterial disease, resistance to fungal disease, resistance to viral disease, modified fatty acid metabolism, modified carbohydrate metabolism, and male sterility.

16. A rice plant, a part thereof, or a rice seed, produced by the method of claim 15, wherein said rice plant, or a part thereof, or rice seed, expresses the desired trait and all of the physiological and morphological characteristics of rice cultivar 'Taurus', as described in the specification, determined at a 5% significance level, when grown in the same environmental conditions.

17. An herbicide resistant rice plant produced by the method of claim 15, wherein the transgene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile, wherein said rice plant expresses herbicide resistance and all of the physiological and morphological characteristics of rice cultivar 'Taurus', as described in the specification, determined at a 5% significance level, when grown in the same environmental conditions.

18. A method of introducing a desired trait into rice cultivar 'Taurus', said method comprising the steps of:
(a) crossing plants as recited in claim 2 with plants of another rice line expressing the desired trait, to produce progeny seeds;
(b) growing the progeny seeds to produce progeny plants and selecting the progeny plants that express the desired trait, to produce selected progeny plants;
(c) crossing the selected progeny plants with plants as recited in claim 2 to produce new progeny plants;
(d) selecting the new progeny plants that express the desired trait; and
(e) repeating steps (c) and (d) three or more times in succession to produce selected higher generation backcross progeny plants that express the desired trait and all of the physiological and morphological characteristics of rice cultivar 'Taurus', as described in the specification, determined at a 5% significance level, when grown in the same environmental conditions.

19. The method of claim 18, additionally comprising the step of planting a plurality of rice seed produced by selecting higher generation backcross progeny plants under conditions favorable for the growth of rice plants and producing rice seed from the resulting rice plants.

20. The rice seed resulting from the method of claim 19, wherein, if the resulting rice seed is grown, then the rice plants grown from the resulting rice seed express the desired trait and all of the physiological and morphological characteristics of rice cultivar 'Taurus', as described in the specification, determined at a 5% significance level, when grown in the same environmental conditions.

* * * * *